US007504378B2

(12) United States Patent
Llinas-Brunet et al.

(10) Patent No.: US 7,504,378 B2
(45) Date of Patent: Mar. 17, 2009

(54) MACROCYCLIC PEPTIDES ACTIVE AGAINST THE HEPATITIS C VIRUS

(75) Inventors: Montse Llinas-Brunet, Dollard-des-Ormeaux (CA); Murray D. Bailey, Pierrefonds (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 332 days.

(21) Appl. No.: 11/298,443

(22) Filed: Dec. 10, 2005

(65) Prior Publication Data
US 2006/0089300 A1    Apr. 27, 2006

Related U.S. Application Data

(63) Continuation of application No. 10/686,755, filed on Oct. 16, 2003, now abandoned.

(60) Provisional application No. 60/421,414, filed on Oct. 25, 2002, provisional application No. 60/433,820, filed on Dec. 16, 2002, provisional application No. 60/442,768, filed on Jan. 27, 2003.

(51) Int. Cl.
| | |
|---|---|
| A61K 38/00 | (2006.01) |
| A61K 31/47 | (2006.01) |
| A61K 38/12 | (2006.01) |
| A01N 43/42 | (2006.01) |
| C07K 5/00 | (2006.01) |
| C07K 7/00 | (2006.01) |
| C07K 16/00 | (2006.01) |
| C07K 17/00 | (2006.01) |
| C07D 225/00 | (2006.01) |
| C07D 295/00 | (2006.01) |

(52) U.S. Cl. ............................ 514/9; 514/312; 530/317; 540/450

(58) Field of Classification Search ................ None
See application file for complete search history.

(56) References Cited

U.S. PATENT DOCUMENTS

| | | | | |
|---|---|---|---|---|
| 5,824,784 A * | 10/1998 | Kinstler et al. | ............. | 530/399 |
| 6,159,938 A | 12/2000 | Gyorkos et al. | | |
| 6,187,905 B1 | 2/2001 | Hurst et al. | | |
| 6,323,180 B1 | 11/2001 | Llinas-Brunet et al. | | |

(Continued)

FOREIGN PATENT DOCUMENTS

| | | |
|---|---|---|
| EP | 1 256 628 A2 | 11/2002 |
| GB | 2 337 262 A | 11/1999 |
| JP | 10-298151 | 11/1998 |
| JP | 11-35478 | 2/1999 |
| JP | 11-127861 | 5/1999 |
| JP | 11-137252 | 5/1999 |
| JP | 11-292840 | 10/1999 |
| JP | 2001-103993 | 4/2001 |
| WO | WO 97/43310 A1 | 11/1997 |
| WO | WO 98/17679 A1 | 4/1998 |
| WO | WO 98/22496 A2 | 5/1998 |

(Continued)

OTHER PUBLICATIONS

Cappelletti et al. New conformationally constrained Xxx-Pro bicyclic mimetics. Letters in Peptide Science. 1995. vol. 2, pp. 161-164.*
Glenn et al. Electron-Impact-Induced Fragemtnation of some isomeric cyclopropyl picolyl and pyridyl ketones. Organic Mass Spectrometry, 1975, vol. 10, pp. 913-918.*
Stephen M. Berge, et al. "Pharmaceutical Salts", Journal of Pharmaceutical Sciences, vol. 66, No. 1, pp. 1-19, Jan. 1977.
Jinkun Huang, et al. "Olefin Metathesis-Active Ruthenium Complexes Bearing a Nucleophilic Carbene Ligand", J. Am. Chem. Soc. 1999, vol. 121, pp. 2674-2678.
Jason S. Kingsbury, et al. "A Recyclable Ru-Based Metathesis Catalyst", J. Am. Chem. Soc. 1999, 121 pp. 791-799.

(Continued)

*Primary Examiner*—Cecilia Tsang
*Assistant Examiner*—Marcela M Cordero Garcia
(74) *Attorney, Agent, or Firm*—Michael P. Morris; Mary-Ellen M. Devlin; Philip I. Datlow

(57) ABSTRACT

Compounds of formula (I):

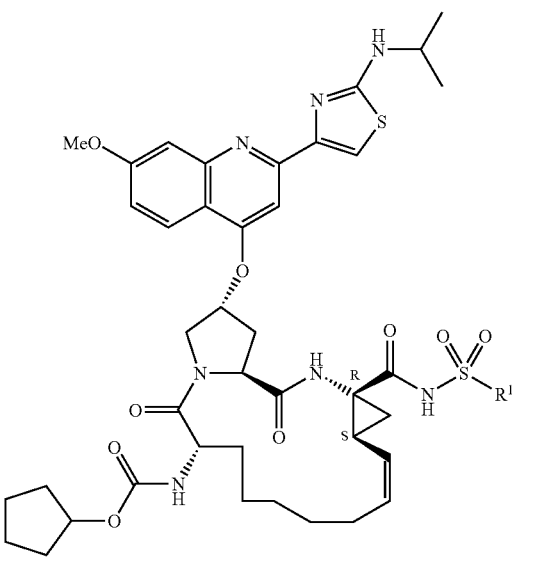

(I)

wherein $R^1$ is $(C_{1-8})$alkyl, $(C_{3-7})$cycloalkyl, $\{(C_{1-6})$alkyl-$(C_{3-7})$cycloalkyl$\}$ or Het, which are all optionally substituted from 1 to 3 times with halo, cyano, nitro, O—$(C_{1-6})$alkyl, amido, amino or phenyl, or $R^1$ is $C_6$ or $C_{10}$ aryl which is optionally substituted from 1 to 3 times with halo, cyano, nitro, $(C_{1-6})$alkyl, O—$(C_{1-6})$alkyl, amido, amino or phenyl; or a pharmaceutically acceptable salt thereof, useful as an inhibitor of the HCV NS3 protease.

25 Claims, No Drawings

U.S. PATENT DOCUMENTS

| | | |
|---|---|---|
| 6,608,027 B1 | 8/2003 | Tsantrizos et al. |
| 6,867,185 B2 | 3/2005 | Campbell et al. |
| 6,869,964 B2 | 3/2005 | Campbell et al. |
| 7,119,072 B2 * | 10/2006 | Llinas-Brunet et al. ........ 514/18 |
| 7,141,574 B2 * | 11/2006 | Beaulieu et al. ............. 514/256 |
| 7,241,801 B2 * | 7/2007 | Beaulieu et al. ............. 514/419 |
| 2003/0181363 A1 | 9/2003 | Llinas-Brunet et al. |
| 2003/0224977 A1 | 12/2003 | Llinas-Brunet et al. |
| 2004/0002448 A1 | 1/2004 | Tsantrizos et al. |
| 2004/0038872 A1 | 2/2004 | Campbell et al. |
| 2004/0138109 A1 | 7/2004 | Chen et al. |
| 2005/0020503 A1 | 1/2005 | Llinas-Brunet et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0222236 A1 * | 10/2005 | Tsantrizos et al. .......... 514/394 |
| 2006/0052418 A1 * | 3/2006 | Beaulieu et al. ............. 514/339 |
| 2006/0089300 A1 * | 4/2006 | Llinas-Brunet et al. ........ 514/9 |
| 2006/0160798 A1 * | 7/2006 | Beaulieu et al. .......... 514/232.5 |
| 2007/0142380 A1 * | 6/2007 | Beaulieu et al. ............. 514/243 |
| 2007/0249629 A1 * | 10/2007 | Beaulieu et al. ............. 514/256 |
| 2008/0221159 A1 * | 9/2008 | Tsantrizos et al. .......... 514/312 |

FOREIGN PATENT DOCUMENTS

| | | |
|---|---|---|
| WO | WO 98/46597 A1 | 10/1998 |
| WO | WO 98/46630 A1 | 10/1998 |
| WO | WO 99/07733 A2 | 2/1999 |
| WO | WO 99/07734 A2 | 2/1999 |
| WO | WO 99/38888 A2 | 8/1999 |
| WO | WO 99/50230 A1 | 10/1999 |
| WO | WO 99/64442 A1 | 12/1999 |
| WO | WO 00/06529 | 2/2000 |
| WO | WO 00/09543 A3 | 2/2000 |
| WO | WO 00/09558 A1 | 2/2000 |
| WO | WO 00/31129 A1 | 2/2000 |
| WO | WO 00/20400 A1 | 4/2000 |
| WO | WO 00/59929 A1 | 10/2000 |
| WO | WO 01/02424 A2 | 1/2001 |
| WO | WO 01/07407 A1 | 2/2001 |
| WO | WO 01/16357 A2 | 3/2001 |
| WO | WO 01/32691 A1 | 5/2001 |
| WO | WO 01/40262 A1 | 6/2001 |
| WO | WO 01/47883 A1 | 7/2001 |
| WO | WO 01/58929 A1 | 8/2001 |
| WO | WO 01/64678 A2 | 9/2001 |
| WO | WO 01/74768 A2 | 10/2001 |
| WO | WO 01/77113 A2 | 10/2001 |
| WO | WO 01/81325 A2 | 11/2001 |
| WO | WO 01/85172 A1 | 11/2001 |
| WO | WO 01/90121 A2 | 11/2001 |
| WO | WO 02/06246 A1 | 1/2002 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/18369 A2 | 3/2002 |
| WO | WO 02/057287 A2 | 7/2002 |
| WO | WO 02/057425 A2 | 7/2002 |
| WO | WO 02/060926 A2 | 8/2002 |
| WO | WO 02/069903 A2 | 9/2002 |
| WO | WO 02/079234 A1 | 10/2002 |
| WO | WO 02/098424 A1 | 12/2002 |
| WO | WO 02/100846 A1 | 12/2002 |
| WO | WO 02/100851 A2 | 12/2002 |
| WO | WO 03/000254 A1 | 1/2003 |
| WO | WO 03/007945 A1 | 1/2003 |
| WO | WO 03/010140 A2 | 2/2003 |
| WO | WO 03/010141 A2 | 2/2003 |
| WO | WO 03/026587 A2 | 4/2003 |
| WO | WO 03/053349 A2 | 7/2003 |
| WO | WO 03/099316 | 12/2003 |

OTHER PUBLICATIONS

Viktor Krchnak, et al. "Polymer-Supported Mitsunobu Ether Formation and its Use in Combinatorial Chemistry", Tetrahedron Letters, vol. 36, No. 35 pp. 6193-6196, 1995.

Scott J. Miller, et al. "Application of Ring-Closing Metathesis to the Synthesis of Rigidified Amino Acids and Peptides", J. Am. Chem. Soc. vol. 118 pp. 9606-9614, 1996.

Thomas A. Rano, et al. "Solid Phase Synthesis of Aryl Ethers Via the Mitsunobu Reaction", Tetrahedron Letters, vol. 36, No. 22 pp. 3789-3792, 1995.

W. Clark Still, et al. "Rapid Chromatographic Technique for Preparative Separations with Moderate Resolution" J. Org. Chem., vol. 43, No. 14, 1978 pp. 2923-2925.

Chemical Abstract: 131:310838 (JP 11292840).
Derwent Abstract: AN 2001-435746 (47) (JP2001103993).
Derwent Abstract: AN 1999-040664 (04) (JP 10298151).
Derwent Abstract: AN 1999-350322 (30) (JP 11127861).
Derwent Abstract: AN 2000-018687 (02) (JP 11292840).
Derwent Abstract: AN 1999-186214 (16) (JP 11035478).
Derwent Abstract: AM 1999-374374 (32) (JP 11137252).
Chemical Abstract: 134:275747 (JP2001103993).
Chemical Abstract: 130:33002 (JP 10298151).
Chemical Abstract: 131:18011 (JP 11127861).

* cited by examiner

MACROCYCLIC PEPTIDES ACTIVE AGAINST THE HEPATITIS C VIRUS

RELATED APPLICATIONS

This Case is a Continuation of U.S. application Ser. No. 10/686,755, filed on Oct. 16, 2003, which claims the benefit of U.S. Provisional Applications, Ser. No. 60/421,414, filed on Oct. 25, 2002, Ser. No. 60/433,820, filed on Dec. 16, 2002 and Ser. No. 60/442,768, filed on Jan. 27, 2003.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

The following is a list of patent application published in the last few years that disclose HCV NS3 protease inhibitor peptide analogs that are structurally different from the compounds of the present invention:

WO 98/17679 (published Apr. 30, 1998); WO 99/50230 (published Oct. 7, 1999); WO 01/74768 (published Oct. 11, 2001); WO 98/22496 (published May 28, 1998); U.S. Pat. No. 6,187,905; WO 97/43310 (published Nov. 20, 1997); WO 01/58929 (published Aug. 16, 2001); WO 01/77113 (published Oct. 18, 2001); WO 01/81325 (published Nov. 1, 2001); WO 98/46597 (published Oct. 22, 1998); WO 98/46630 (published Oct. 22, 1998); JP 10298151 (published Nov. 10, 1998); JP 11127861 (published May 18, 1999); JP 2001103993 (published Apr. 17, 2001); JP 11292840 (published Oct. 26, 1999); WO 99/38888 (published Aug. 5, 1999); WO 99/64442 (published Dec. 16, 1999); WO 00/31129 (published Jun. 2, 2000); WO 01/32691 (published May 10, 2001); U.S. Pat. No. 6,159,938 (published Dec. 12, 2000): WO 01/02424 (published Jan. 11, 2001); WO 01/07407 (published Feb. 1, 2001); WO 01/40262 (published Jun. 7, 2001); and WO 01/64678 (published Sep. 7, 2001).

Peptide analogs which inhibit the HCV NS3 protease have been disclosed in WO 00/09543 (published Feb. 24, 2000), WO 00/09558 (published Feb. 24, 2002), WO 00/59929 (published Oct. 12, 2000) and WO 02/060926 (published Aug. 8, 2002). The compounds of the present invention distinguish themselves by having a different chemical structure and by the surprising finding that they specifically inhibit HCV NS3 protease while showing insignificant inhibitory activity against other serine proteases. The WO 00/59929 discloses the corresponding terminal acid of the present compounds, which also exhibit specificity. WO 03/053349 published on Jul. 3, 2003 also discloses macrocyclic tripeptide inhibitors of hepatitis C virus. Nevertheless, the specific activity of the present compounds was unexpected.

One advantage of the present invention is that it provides tripeptide compounds that are inhibitory to the NS3 protease, an enzyme essential for the replication of the hepatitis C virus.

A further advantage of one aspect of the present invention resides in the fact that the compounds specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

Furthermore, the compounds are active in cell culture.

SUMMARY OF THE INVENTION

Included in the scope of the invention are compounds of formula (I):

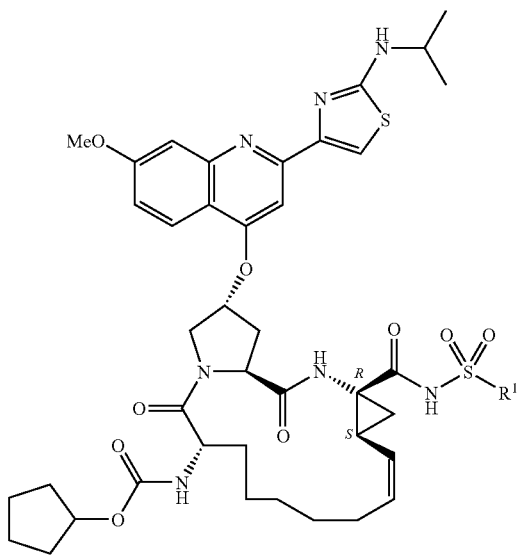

(I)

wherein $R^1$ is $(C_{1-8})$alkyl, $(C_{3-7})$cycloalkyl, $\{(C_{1-6})$alkyl-$(C_{3-7})$cycloalkyl$\}$ or Het, which are all optionally substituted from 1 to 3 times with halo, cyano, nitro, O—$(C_{1-6})$alkyl, amido, amino or phenyl, or $R^1$ is $C_6$ or $C_{10}$ aryl which is optionally substituted from 1 to 3 times with halo, cyano, nitro, $(C_{1-6})$alkyl, O—$(C_{1-6})$alkyl, amido, amino or phenyl; or a pharmaceutically acceptable salt thereof.

Included within the scope of this invention is a pharmaceutical composition comprising an anti-hepatitis C virally effective amount of a compound of formula I, or a pharmaceutically acceptable salt thereof, in admixture with a pharmaceutically acceptable carrier medium or auxiliary agent.

Also within the scope of this invention is the use of a compound of formula I, as described herein, for the manufacture of a medicament for the treatment or prevention of hepatitis C viral infection.

According to one embodiment, the pharmaceutical composition of this invention further comprises interferon or pegylated-interferon. Alternatively, the composition comprises a compound of formula (I) in combination with Ribavirin. As a further alternative, the composition comprises a compound of formula (I) in combination with interferon (pegylated or not) and ribavirin.

An important aspect involves a method of inhibiting the replication of hepatitis C virus by exposing the virus to a hepatitis C NS3 protease-inhibiting amount of a compound of formula (I), or a pharmaceutically acceptable salt thereof or a composition as described above.

Another important aspect of the invention involves a method of treating or preventing a hepatitis C viral infection in a mammal by administering to the mammal an anti-hepatitis C virally effective amount of a compound of formula I, a pharmaceutically acceptable salt thereof, or a composition as described above, alone or in combination with interferon or ribavirin or both.

DETAILED DESCRIPTION OF PREFERRED EMBODIMENTS

Definitions

As used herein, the following definitions apply unless otherwise noted: With reference to the instances where (R) or (S) is used to designate the absolute configuration of a substituent, e.g. $R^4$ of the compound of formula I, the designation is done in the context of the whole compound and not in the context of the substituent alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249-264 (1970)).

As used herein the term "(1R, 2S)-vinyl-ACCA" refers to a compound of formula:

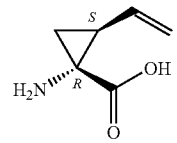

namely, (1R, 2S) 1-amino-2-ethenylcyclopropylcarboxylic acid.

The term "halo" as used herein means a halogen substituent selected from bromo, chloro, fluoro or iodo.

The term "$(C_{1-8})$alkyl" as used herein, either alone or in combination with another substituent, means acyclic, straight or branched chain alkyl substituents containing from 1 to 8 carbon atoms and includes, for example, methyl, ethyl, propyl, butyl, hexyl, 1-methylethyl, 1-methylpropyl, 2-methylpropyl, 1,1-dimethylethyl.

The term "$(C_{3-7})$cycloalkyl" as used herein, either alone or in combination with another substituent, means a cycloalkyl substituent containing from three to seven carbon atoms and includes cyclopropyl, cyclobutyl, cyclopentyl, cyclohexyl and cycloheptyl.

The term "$\{(C_{1-6})$alkyl-$(C_{3-7})$cycloalkyl$\}$" as used herein means a cycloalkyl radical containing from 3 to 6 carbon atoms directly linked to an alkylene radical containing 1 to 7 carbon atoms; for example, cyclopropylmethyl, cyclopentylethyl, cyclohexylmethyl, and cyclohexylethyl. In the instance where $R^1$ is a $\{(C_{1-6})$alkyl-$(C_{3-7})$cycloalkyl$\}$, this group is attached to the $SO_2$ group via the $(C_{1-6})$alkyl (i.e. the alkylene portion).

The term "O—$(C_{1-6})$alkyl" or "$C_{1-6}$-alkoxy" as used herein interchangeably, either alone or in combination with another substituent, means the substituent —O—(C$_{1-6}$)alkyl wherein alkyl is as defined above containing up to six carbon atoms. O—(C$_{1-6}$)alkyl includes methoxy, ethoxy, propoxy, 1-methylethoxy, butoxy and 1,1-dimethylethoxy. The latter substituent is known commonly as tert-butoxy.

The term "Het" as used herein, either alone or in combination with another substituent, means a monovalent substituent derived by removal of a hydrogen from a five-, six-, or seven-membered saturated or unsaturated (including aromatic) heterocycle containing from one to four heteroatoms selected from nitrogen, oxygen and sulfur. Examples of suitable heterocycles include: tetrahydrofuran, thiophene, diazepine, isoxazole, piperidine, dioxane, pyrimidine or

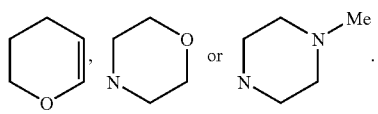

The term "Het" also includes a heterocycle as defined above fused to one or more other cycle be it a heterocycle or any other cycle. One such examples includes thiazolo[4,5-b]-pyridine.

Although generally covered under the term "Het", the term "heteroaryl" as used herein precisely defines an unsaturated heterocycle for which the double bonds form an aromatic system. Suitable example of heteroaromatic system include: quinoline, indole, pyridine,

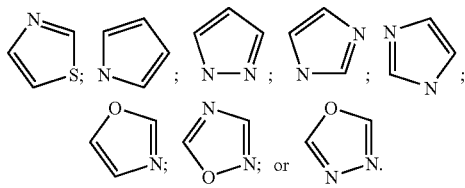

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "immunomodulatory agent" as used herein means those agents (compounds or biologicals) that are effective to enhance or potentiate the immune system response in a mammal. Immunomodulatory agents include, for example, class I interferons (such as α-, β-, δ- and omega interferons, tau-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929 or WO 02/060926, and the Vertex pre-development candidate identified as VX-950. Particularly, compounds # 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926, can be used in combination with the compounds of the present invention.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. Application No. 60/441,674 filed Jan. 22, 2003, herein incorporated by reference in its entirety (Boehringer Ingelheim),
  U.S. Application No. 60/441,871 filed Jan. 22, 2003, herein incorporated by reference in its entirety (Boehringer Ingelheim),
  U.S. application Ser. No. 10/198,680 filed 18 Jul. 2002, herein incorporated by reference in its entirety, which corresponds to WO 03/010140 (Boehringer Ingelheim),
  U.S. application Ser. No. 10/198,384 filed 18 Jul. 2002, herein incorporated by reference in its entirety, which corresponds to WO 03/010141 (Boehringer Ingelheim),
  U.S. application Ser. No. 10/198,259 filed 18 Jul. 2002, herein incorporated by reference in its entirety, which corresponds to WO 03/007945 (Boehringer Ingelheim),
  WO 03/026587 (Bristol Myers Squibb);
  WO 02/100846 A1 and WO 02/100851 A2 (both Shire),
  WO 01/85172 A1 and WO 02/098424 A1 (both GSK),
  WO 00/06529 and WO 02/06246 A1 (both Merck),
  WO 01/47883 and WO 03/000254 (both Japan Tobacco) and
  EP 1 256 628 A2 (Agouron).

Furthermore other inhibitors of HCV polymerase also include nucleoside analogs, for example, those compounds described in:
  WO 01/90121 A2 (Idenix),
  WO 02/069903 A2 (Biocryst Pharmaceuticals Inc.), and
  WO 02/057287 A2 and WO 02/057425 A2 (both Merck/Isis).

Specific examples of inhibitors of an HCV polymerase, include JTK-002/003 and JTK-109 (Japan Tobacco), and NM283 from Idenix.

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from a helicase, an HCV NS2/3 protease and an internal ribosome entry site (IRES). Specific examples of inhibitors of another target in the HCV life cycle include ISIS-14803 (ISIS Pharmaceuticals).

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type 1. This includes both naturally and synthetically produced class I interferons. Examples of class I interferons include α-, β-, δ-, omega interferons, tau-interferons, consensus interferons, asialo-interferons.

The term "class II interferon" as used herein means an interferon selected from a group of interferons that all bind to receptor type I. Examples of class II interferons include γ-interferons.

The pharmaceutical compositions of the invention may contain one or more additional active agents selected, for example, from antiviral agents, immunomodulatory agents, inhibitors of HCV polymerase, other inhibitors of HCV NS3 protease, inhibitors of another target in the HCV life cycle, HIV inhibitors, HAV inhibitors and HBV inhibitors. Examples of such agents are provided in the Definitions section above.

Specific preferred examples of some of these agents are listed below:
(1) antiviral agents: ribavirin and amantadine.
(2) immunomodulatory agents: class I interferons, class II interferons and pegylated interferons.
(3) inhibitors of HCV polymerase: non-nucleosides and nucleoside analogs.
(4) inhibitor of another target in the HCV life cycle that inhibits a target selected from: NS3 helicase, HCV NS2/3 protease or internal ribosome entry site (IRES).
(5) HIV inhibitors: nucleosidic inhibitors, non-nucleosidic inhibitors, protease inhibitors, fusion inhibitors and integrase inhibitors.
(6) HBV inhibitors: agents that inhibit HBV viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, an inhibitor of HCV polymerase, another inhibitor of HCV NS3 protease, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

Preferred Embodiments

Preferably, a compound of formula I is as defined above wherein $R^1$ is $(C_{1-6})$alkyl, $(C_{3-6})$cycloalkyl, $\{(C_{1-6})$alkyl-$(C_{3-6})$cycloalky$\}$ or Het, which are all optionally substituted 1 to 3 times with halo, nitro or O—$(C_{1-6})$alkyl, or phenyl which is optionally substituted from 1 to 3 times with halo, nitro, $(C_{1-6})$alkyl or O—$(C_{1-6})$alkyl.

Preferably, Het is selected from: a heteroaryl selected from:

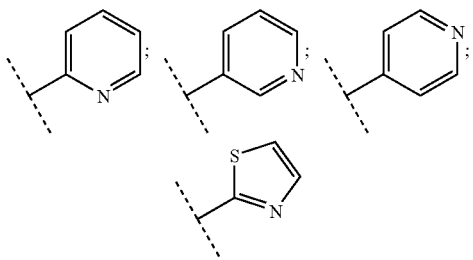

said heteroaryl optionally substituted with $C_{1-6}$ alkyl; or a heterocycle selected from:

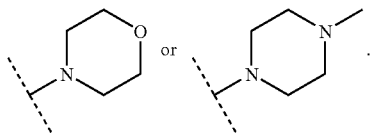

More preferably, a compound of formula I is as defined above wherein $R^1$ is $(C_{1-6})$alkyl, $(C_{3-6})$cycloalkyl, or $\{(C_{1-6})$alkyl-$(C_{3-6})$cycloalkyl$\}$, which are all optionally substituted 1 to 3 times with halo, nitro or O—$(C_{1-6})$alkyl, or phenyl which is optionally substituted from 1 to 3 times with halo, nitro, $(C_{1-6})$alkyl or O—$(C_{1-6})$alkyl.

More preferably, $R^1$ is selected from: methyl, ethyl, n-propyl, i-propyl, n-butyl, sec-butyl, n-pentyl, 2-Me-butyl, 3-Me-butyl, cyclopropyl, cyclobutyl, cyclopentyl, cyclopropylmethyl, cyclohexylethyl, $CCl_3$, $CF_3$, phenyl, 2-fluorophenyl, or 4-methylphenyl.

Even more preferably, $R^1$ is selected from: methyl, ethyl, n-propyl, i-propyl, cyclopropyl, cyclobutyl, cyclopentyl, cyclopropylmethyl, cyclohexylethyl, $CCl_3$, $CF_3$, phenyl, 2-fluorophenyl, or 4-methylphenyl.

Most preferably, $R^1$ is methyl, cyclopropyl, $CF_3$ or phenyl. Again most preferably, $R^1$ is methyl, cyclopropyl or phenyl. Still, most preferably, $R^1$ is methyl. Alternatively, most preferably, $R^1$ is cyclopropyl. Again most preferably, $R^1$ is phenyl.

According to an alternate embodiment, the pharmaceutical composition of this invention may additionally comprise another anti-HCV agent. Examples of anti-HCV agents include, α-(alpha), β-(beta), δ-(delta), γ-(gamma) or ω-(omega) interferon, ribavirin and amantadine.

According to another alternate embodiment, the pharmaceutical composition of this invention may additionally comprise an inhibitor of HCV polymerase.

According to another alternate embodiment, the pharmaceutical composition of this invention may additionally comprise another inhibitor of HCV NS3 protease.

According to yet another alternate embodiment, the pharmaceutical composition of this invention may additionally comprise an inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with other anti-HCV agents which include, but are not limited to: α-, β-, δ-, ω-, or γ-interferon, ribavirin, amantadine; inhibitors of HCV polymerase; other inhibitors of HCV NS3 protease; inhibitors of other targets in the HCV life cycle, which include but not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I.

In a preferred embodiment, this method is useful in decreasing the NS3 protease activity of the hepatitis C virus infecting a mammal.

If the pharmaceutical composition comprises only a compound of this invention as the active component, such method may additionally comprise the step of administering to said mammal one or more other anti-HCV agents selected from an immunomodulatory agent, an antiviral agent, a HCV polymerase inhibitor, a HCV NS3 protease inhibitor, or an inhibitor of other targets in the HCV life cycle such as helicase, NS2/3 protease or IRES. Such additional agents may be administered to the mammal prior to, concurrently with, or following the administration of the composition of this invention.

A compound of formula I set forth herein may also be used as a laboratory reagent. A compound of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula I set forth herein may also be used as a research reagent. A compound of formula I may also be used as positive control to validate surrogate cell-based assays or in vitro or in vivo viral replication assays.

Further details of the invention are illustrated in the following examples which are understood to be non-limiting with respect to the appended claims.

Methodology

In general, the compound of formula I and intermediates therefore are prepared by known methods using reaction conditions which are known to be suitable for the reactants. Several such methods are disclosed in WO 00/09543 and WO 00/09558 incorporated herein by reference.

The following scheme illustrates a convenient process using known methods for preparing a key intermediate of formula 6a from acyclic intermediates:

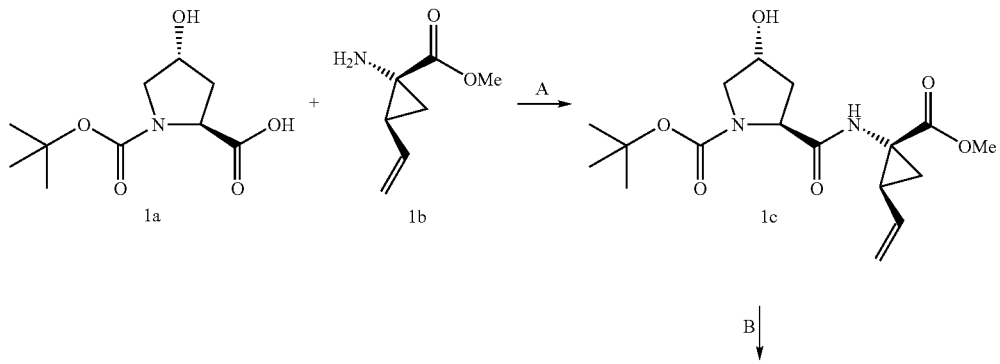

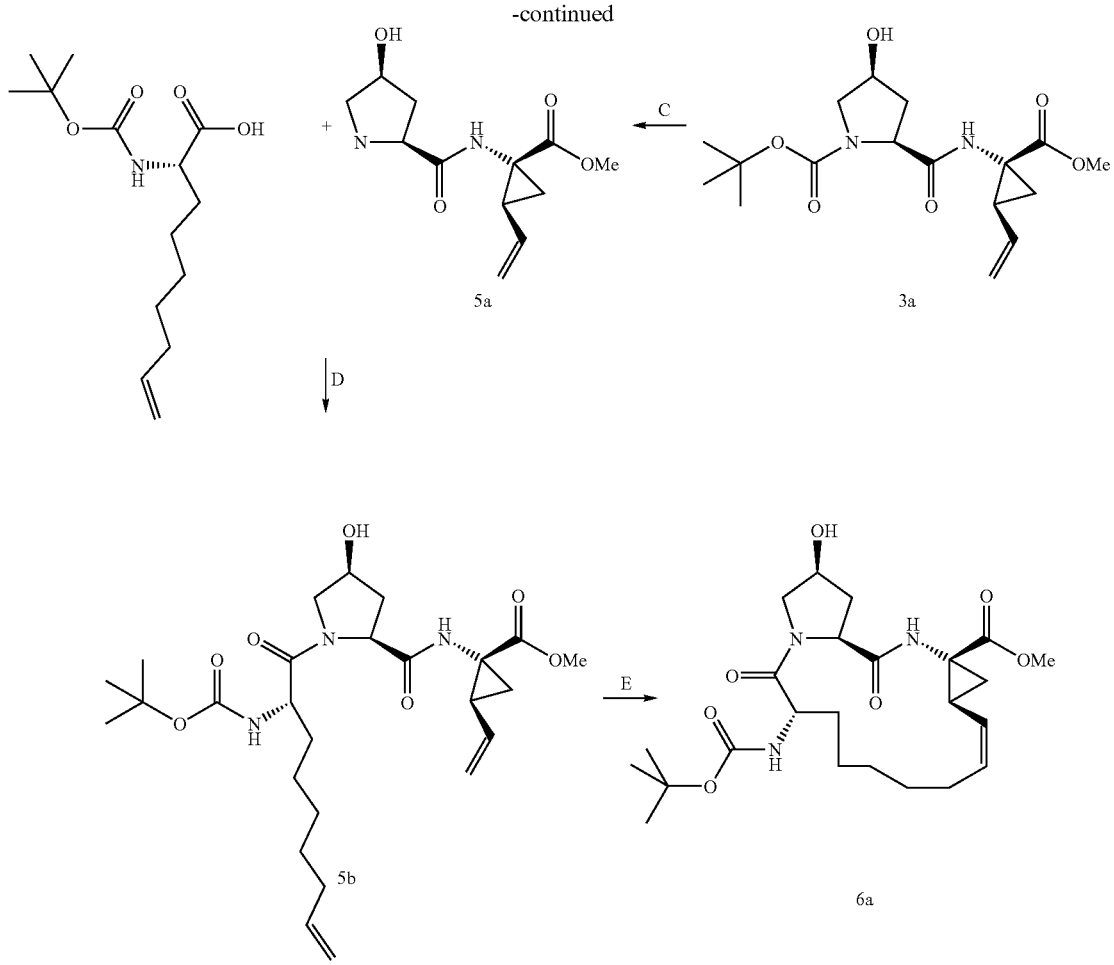

Scheme I:

There are several ways in which the coupling sequences A and C can be carried out which can be easily recognized by persons skilled in the art. Starting with 4-(S)-hydroxyproline, the substituent at the 4-hydroxy can be incorporated via a Mitsunobu reaction (as described in Mitsunobu *Synthesis* 1981, Jan. 1-28; Rano et al. *Tet. Lett.* 1994, 36, 3779-3792; Krchnak et al. *Tet. Lett.* 1995, 36, 6193-6196) before or after the macrocyclization. Alternatively the assembly can be done with the required 4-(R)-hydroxy-substituted proline as disclosed in the general processes of WO 00/09543 & WO 00/09558.

Steps A, B, C, D: Briefly, the P1, P2, and P3 moieties can be linked by well known peptide coupling techniques generally disclosed in WO 00/09543 & WO 00/09558.

Step E: The formation of the macrocycle can be carried out via an olefin metathesis using a Ru-based catalyst such as the one reported by Miller, S. J.; Blackwell, H. E.; Grubbs, R. H. *J. Am. Chem. Soc.* 1996, 118, 9606-9614 (a); Kingsbury, J. S.; Harrity, J. P. A.; Bonitatebus, P. J.; Hoveyda, A. H. *J. Am. Chem. Soc.* 1999, 121, 791-799 (b) and Huang, J.; Stevens, E. D.; Nolan, S. P.; Petersen, J. L.; *J. Am. Chem. Soc.* 1999, 121, 2674-2678 (c). It will also be recognized that catalysts containing other transition metals such as Mo can be used for this reaction.

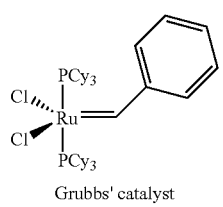

(a)

Grubbs' catalyst

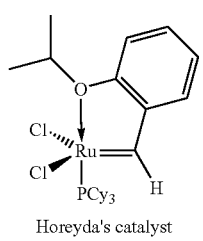

(b)

Horeyda's catalyst

-continued

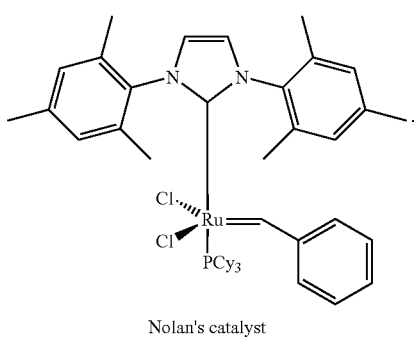

Nolan's catalyst

Subsequent conversion of the key intermediate of formula 6a to the compounds of formula 1 of this invention is disclosed in detail in the examples hereinafter.

EXAMPLES

The present invention is illustrated in further detail by the following non-limiting examples. Other specific ways of synthesis or resolution can be found in WO 00/09543 & WO 00/09558 and in co-pending application Ser. Nos. 09/368,670 and 09/368,866, all of which are hereby incorporated by reference.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million and are referenced to the internal deuterated solvent unless otherwise indicated. The NMR spectra of all final compounds (inhibitors) was recorded in DMSO-$d_6$ of their TFA salt unless otherwise indicated. Flash column chromatography was carried out on silica gel ($SiO_2$) according to Still's flash chromatography technique (W. C. Still et al., *J. Org. Chem.*, 1978, 43, 2923).

Abbreviations used in the examples include vinyl-ACCA: 1-amino-2-vinyl cyclopropylcarboxylic acid; Boc: tert-butyloxycarbonyl [$Me_3COC(O)$]; BSA: bovine serum albumin; Cbz: benzyloxycarbonyl; CHAPS: 3-[(3-cholamidopropyl)-dimethylammonio]-1-propanesulfonate; DBU: 1,8-Diazabicyclo[5.4.0]undec-7-ene; DCM: $CH_2Cl_2$: methylene chloride; DEAD: diethylazodicarboxylate; DIAD: diisopropylazodicarboxylate; DIPEA: diisopropylethylamine; DMAP: dimethylaminopyridine; DMF: N,N-dimethylformamide; DMSO: dimethylsulfoxide; DPPA: diphenylphosphoryl azide; EDTA: ethylenediamine tetraacetic acid; (S,S)-Et-DUPHOS Rh (COD)OTf: (+)-1,2-bis (2S,5S)-2,5-diethylphospholano) benzene (cyctooctadiene) rhodinium (1) trifluoromethanesulfonate; EtOH: ethanol; EtOAc: ethyl acetate; ESMS: electrospray mass spectrometry; eq.: equivalent(s); h.: hour(s); HATU: O-(7-azabenzotriazol-1-yl)-1,1,3,3-tetramethyluronium hexafluorophosphate; HPLC: high performance liquid chromatography; MS: mass spectrometry; MALDI-TOF: Matrix Assisted Laser Disorption Ionization-Time of Flight; min.: minute(s); FAB: Fast Atom Bombardment; Me: methyl; MeOH: methanol; Ph: phenyl; Pr: propyl; RP-HPLC: reverse phase HPLC; Rt: retention time; RT: room temperature (18°-22°); sat.: saturated; TBTU: 2-(1H-benzotriazole-1-yl)-1,1,3,3-tetramethyluronium tetrafluoroborate; TFA: trifluoroacetic acid; THF: tetrahydrofuran; TLC: thin layer chromatography; Tris/HCl: tris(hydroxymethyl)aminomethane hydrochloride.

Example 1

Synthesis of Dipeptide 1c

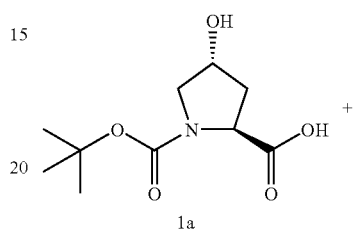

1a

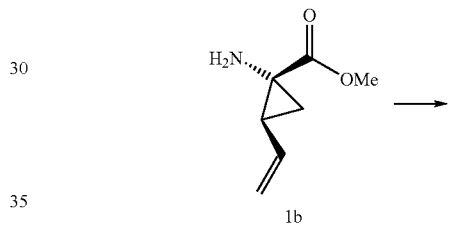

1b

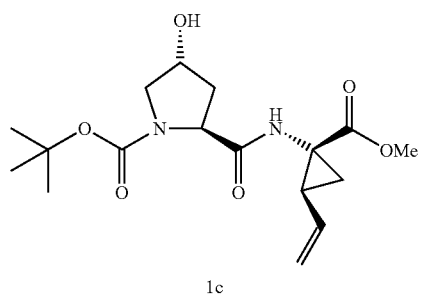

1c

A mixture of Boc-hydroxyproline 1a (50.0 g, 216 mmol), (1R,2S)-vinyl-ACCA hydrochloride 1b (42.25 g, 238 mmol), TBTU (76.36 g, 238 mmol) and DIPEA (113 mL, 649 mmol) in DMF (800 mL) was stirred at R.T. under a nitrogen atmosphere. After 3.5 h, the solvent was evaporated and the residue extracted with EtOAc and washed with hydrochloric acid (10%), saturated sodium bicarbonate and brine. The organic phase was then dried over magnesium sulfate, filtered and evaporated to afford an oil. Drying the oil overnight (18 h) under high vacuum gave the dipeptide 1c as a yellow foam (72.0 g, 94%, purity >95% by HPLC).

Example 2

Synthesis of Dipeptide 2a

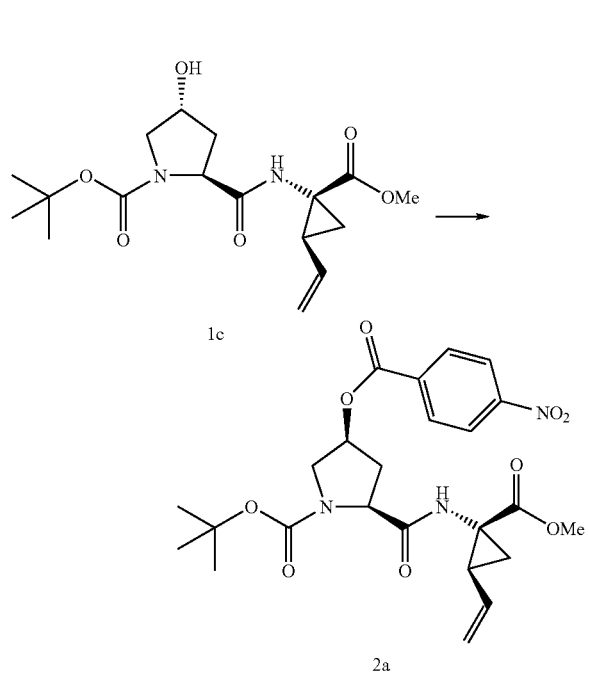

The dipeptide 1c (72.0 g, 203 mmol), triphenylphosphine (63.94 g, 243.8 mmol, 1.2 equiv.) and 4-nitrobenzoic acid (41.08 g, 245.8 mmol, 1.2 equiv) were dissolved in dry THF (1.4 L) and the stirred solution cooled to 0° under a nitrogen atmosphere. DEAD (38.4 mL, 244 mmol, 1.2 equiv.) was then added dropwise over 45 min and the reaction allowed to warm to R.T. After 4 h, the solvent was evaporated and the residue divided into four portions. Each of these was chromatographed over fine silica gel (10-40 μm mesh, column diameter 12 cm, column length 16 cm) using a gradient of 2:1 hexane/EtOAc to 1:1 hexane/EtOAc to pure EtOAc. Ester 2a was obtained as an amorphous white solid after evaporation of the solvents and drying under high vacuum at 70° for 1 h (108.1 g, quantitative yield).

Example 3

Synthesis of Alcohol Dipeptide 3a

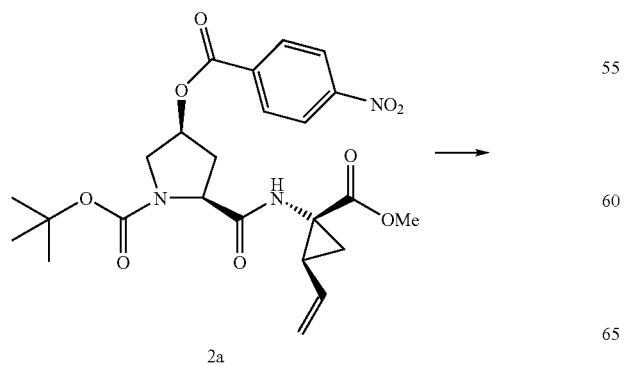

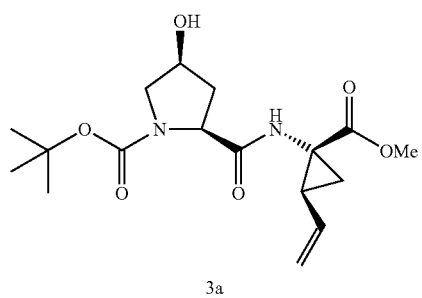

The nitrobenzoyl ester 2a (108.1 g, 203.1 mmol) was dissolved in THF (1.0 L) and the resulting solution cooled to 0°. A solution of lithium hydroxide monohydrate (10.66 g, 253.9 mmol) in water (225 mL) was then added rapidly and the reaction stirred at 0° for 30 min. after which time the remaining base was neutralized with hydrochloric acid (1N, 50.8 mL). Additional acid was slowly added until the yellow color dissipated (7 mL). The resulting mixture was then evaporated and the residue extracted with EtOAc (3×150 mL) and washed with saturated sodium bicarbonate (150 mL) and brine (150 mL). The organic phase was dried over magnesium sulfate-charcoal, filtered through diatomaceous earth and evaporated. Overnight drying of the residue under high vacuum yielded the alcohol 3a as a colorless foam (70.1 g, 98%, purity>99% by HPLC).

Example 4

Synthesis of (2S)-N-Boc-amino-non-8-enoic Acid (4c)

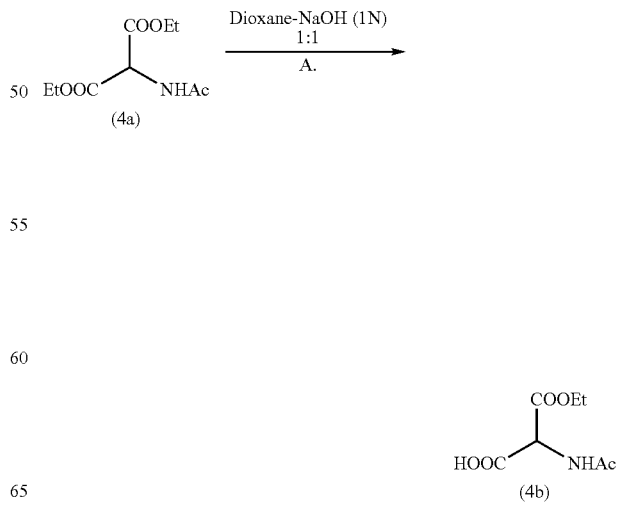

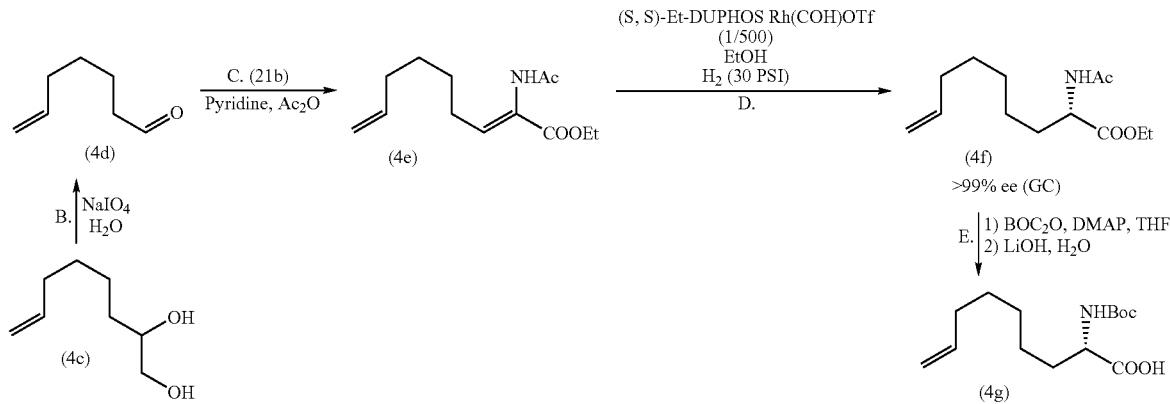

Step A. To a solution of commercially available diethyl 2-acetamidomalonate 4a (100 g, 0.46 mole) in dioxane (500 mL) was added aqueous sodium hydroxide (1M, 1 eq., 460 mL) dropwise over 30 to 45 min. The resulting mixture was left to stir for 16.5 h, then dioxane was evaporated in vacuo. The resulting aqueous solution was extracted with three portions of 300 mL of EtOAc and acidified to pH 1 with concentrated HCl. This solution was left to crystallize in an ice-water bath. After the appearance of a few crystals, the mixture was sonicated and an abundant precipitate appeared. Filtration and drying under vacuum afforded compound 4b, (62.52 g, 72% yield) as a white solid.

Step B. To a magnetically stirred emulsion of commercially available 7-octene-1,2-diol 4c (25 g, 0.173 mole) and $H_2O$ (100 mL), in a 1 L round bottom flask, an aqueous solution of sodium periodate (40.7 g, 0.190 moles, 1.1 eq., in 475 mL $H_2O$) was added over a period of 20 min (slightly exothermic). The resulting mixture was stirred at room temperature for an additional 1 h (completion of reaction confirmed by TLC). The mixture was then decanted in a separatory funnel and the aqueous layer was separated from the organic layer. The aqueous solution was saturated with NaCl, decanted and separated from the organic fraction once more. The two organic fractions were combined, dried with sodium sulfate and filtered over a cotton plug (in a Pasteur pipette) to give compound 4d (15.135 g, colorless oil, 78% yield). The aqueous solution was extracted with $CH_2Cl_2$, dried with anhydrous $MgSO_4$, and concentrated under vacuum (without heating, i.e. 6-heptanal b.p. 153° C.) to obtain an additional amount of compound 4d (1.957 g, colorless oil, 10% yield). Total yield 88%.

Step C. To solid ethyl 2-acetamidomalonate 4b (7.57 g, 40 mmol.) was added 6-heptenal 4d (4.48 g, 40 mmol) in solution in pyridine (32 mL, 10 eq) over 1 min. The resulting solution was cooled in a 10° bath and acetic anhydride (12 mL, 3.2 eq.) was added over 4 min. The resulting orange solution was stirred for 3 h at RT and another portion of ethyl 2-acetamidomalonate 4b (2.27 g) was added. The resulting mixture was stirred at room temperature for an extra 11 h. Ice (60 mL) was then added and the solution was stirred for 1.5 h, then the mixture was diluted with 250 mL of water and extracted with two portions of diethyl ether. The etheral solution was washed with 1N HCl, sat. $NaHCO_3$, dried $Na_2SO_4$, concentrated and purified by flash chromatography (EtOAc 40%/hexane) to give compound 4e (4.8 g, 50% yield) as a pale yellow oil.

Step D. To a degassed (argon bubbling for 30 min.) solution of Z-ethyl 2-acetamido-2,8-nonadienoate 4e (8.38 g, 35 mmol) in dry ethanol (70 mL) was added (S,S)-Et-DUPHOS Rh(COD)OTf (51 mg, (substrate/catalyst=496). The mixture was put under 30 psi of hydrogen (after 4 vacuum-$H_2$ cycles) and stirred on a Parr shaker for 2 h. The resulting mixture was evaporated to dryness to obtain the crude compound 4f, which was used in the subsequent step without purification.

Step E. To a solution of crude (S)-ethyl 2-acetamido-8-nonenoate 4f (7.3 g, 30.3 mmol) in THF (100 mL), $Boc_2O$ (13.2 g, 2 eq.) and DMAP (740 mg, 0.2 eq) were added. The reaction mixture was heated at reflux for 2.5 h. Subsequently, most of the THF solvent was evaporated, the crude mixture was diluted with $CH_2Cl_2$ and washed with 1 N HCl in order to remove the DMAP. The organic layer was further extracted with saturated aqueous $NaHCO_3$, dried with anhydrous $Na_2SO_4$ and concentrated under vacuum. The crude product was then diluted with THF (50 mL) and water (30 mL), $LiOH.H_2O$ (2.54 g, 2 eq.) was added and the resulting mixture was stirred at RT for 25 h (completion of the hydrolysis was confirmed by TLC). The reaction mixture was concentrated under vacuum to remove most of the THF solvent and diluted with $CH_2Cl_2$. The resulting solution was washed with 1 N HCl, dried with anhydrous $Na_2SO_4$ and concentrated under vacuum. In order to remove minor impurities and excess $Boc_2O$, the crude product was purified by flash chromatography (using a solvent gradient from 100% hexane—100% EtOAc as the eluent). The titled compound 4g was obtained in high purity as a pale yellow oil (5.82 g, 71% yield). $^1H$ NMR (DMSO, 400 MHz): δ 7.01 (d, J=8 Hz, 1H), 5.79 (tdd, Jt=6.7 Hz, Jd=17.0, 10.2 Hz, 1H), 5.00 (md, Jd=17.0 Hz, 1H), 4.93 (md, Jd=10.2 Hz, 1H), 3.83 (m, 1H), 2.00 (q, J=6.9 Hz, 2H), 1.65-1.5 (m, 2H), 1.38 (s, 9H), 1.35-1.21 (m, 6H).

Example 5

Synthesis of Tripeptide 5b

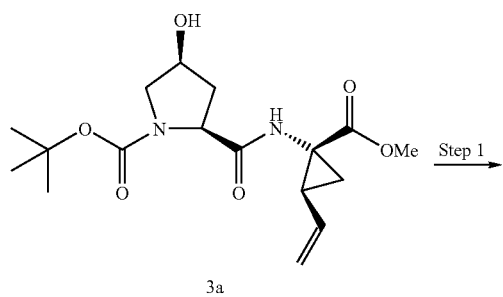

3a

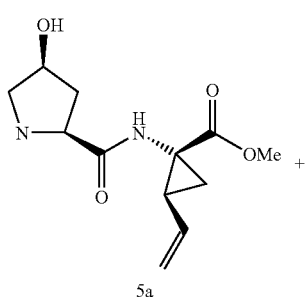

5a

Step 1: A solution of hydrogen chloride in dioxane (4N, Aldrich) was added to the Boc P2-P1 fragment 3a (5.32 g, 15.0 mmol) resulting in a colorless solution. After 1 h of stirring at room temperature, the solvent was evaporated and the residue placed under high vacuum for 3 h which afforded the hydrochloride salt of compound 5a as an amorphous solid which was used as such.

Step 2: DIPEA (2.6 mL, 15 mmol) was added to a mixture of the above prepared P1-P2 hydrochloride (15 mmol) in dry DCM (100 mL) resulting in a homogeneous solution. Separately, TBTU (5.30 g, 16.5 mmol. 1.1 equiv.) was added to a stirred solution of C9-linker 4g (4.07 g, 15.0 mmol) in dry DCM (130 mL) resulting in partial dissolution of the reagent. DIPEA (2.6 mL, 15 mmol) was added resulting in an essentially homogeneous solution after 10 min. To this was then added the P1-P2 solution and DIPEA added until the reaction was basic (pH>8 on wet litmus). After stirring under a nitrogen atmosphere for 5 h, the solvent was evaporated and the residue extracted with EtOAc (2×250 mL) and washed with dilute hydrochloric acid (0.05N, 400 mL), water (400 mL), and saturated sodium bicarbonate (400 mL). The combined organic phases were then dried over magnesium sulfate, filtered and evaporated to a yellow syrup. The crude product was chromatographed over silica gel using 6:1 EtOAc/hexane to pure EtOAc as eluent, which afforded the desired tripeptide, diene 5b, as a white foam (5.88 g, 82%, purity>95% by HPLC).

Example 6

Synthesis of Macrocyclic Intermediate 6a

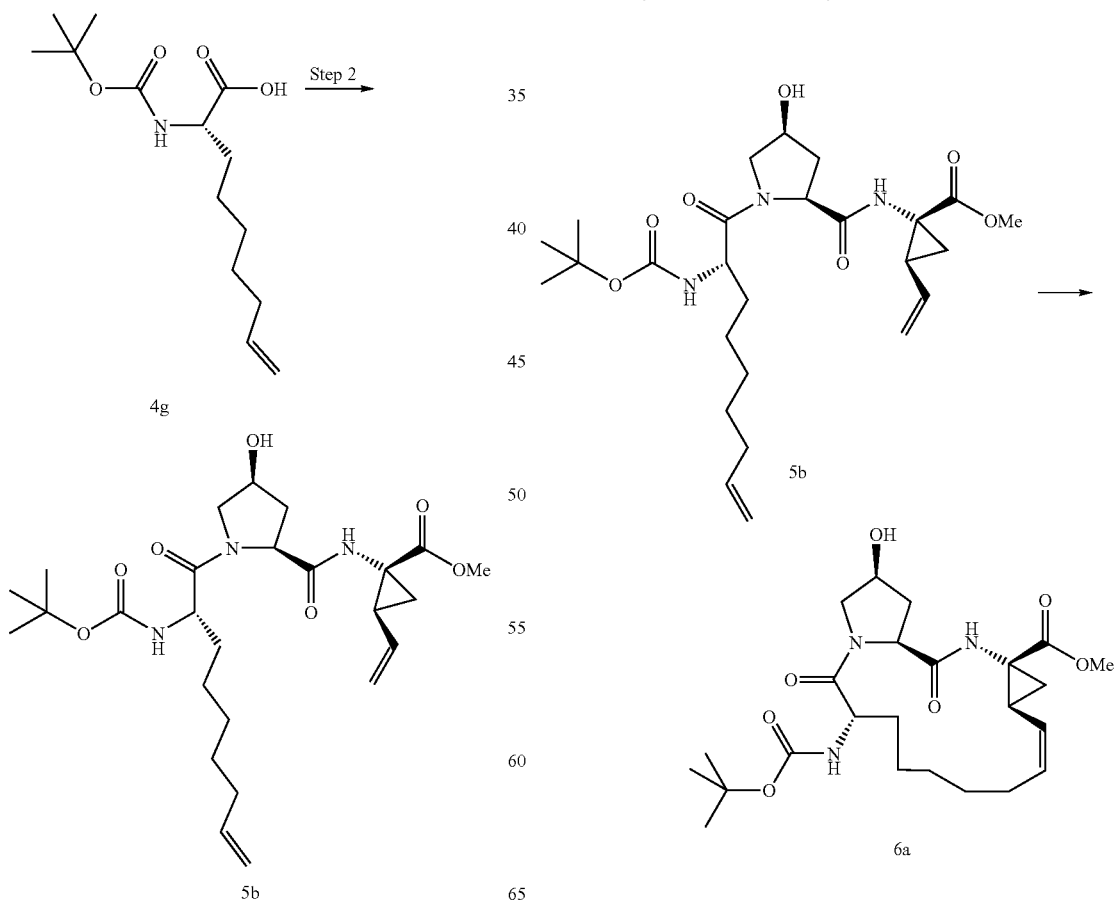

A solution of diene 5b (4.0 g, 7.88 mmol) in dry DCM (800 mL) was deoxygenated by bubbling Ar for 2 h. Hoveyda's catalyst (262 mg, 0.434 mmol, 5.5 mol %) was then added as a solid and the reaction was refluxed under an Ar balloon. After 28 h, the red-orange solution was evaporated to an amorphous solid and then purified by flash column chromatography over silica gel. The initial solvent system was 10% EtOAc in CH$_2$Cl$_2$. Once the catalyst was eluted from the column, the solvent was changed to pure EtOAc. Elution of the catalyst from the column was evident from its color. The macrocyclic product 6a was isolated as a colorless foam which was re-dissolved in CH$_2$Cl$_2$/hexane (~1:2). Evaporation of the solvent afforded a white powder (3.362 g, 89% yield).

$^1$H NMR (CDCl$_3$, 400 MHz): δ 1.20-1.50 (m, 6H), 1.43 (s, 9H), 1.53 (dd, J=9.5 & 5.4, 1H), 1.61-1.70 (m, 1 H), 1.76-1.90 (m, 2H), 2.05-2.26 (m, 4H), 2.45 (d, J=14.3, 1H), 3.67 (s, 3H), 3.71 (d, J=11.1, 1H), 3.90 (dd, J=11.1 & 4.3, 1H), 4.43-4.53 (m, 2H), 4.76 (d, J=8.6, 1H), 4.86 (bd, J=9.8, 1H), 5.20-5.23 (m, 2H), 5.57 (dt, J=7.0 & 9.8, 1H), 7.32 (bs, 1H).

Example 7

Synthesis of Macrocyclic Tripeptide Intermediate 7h

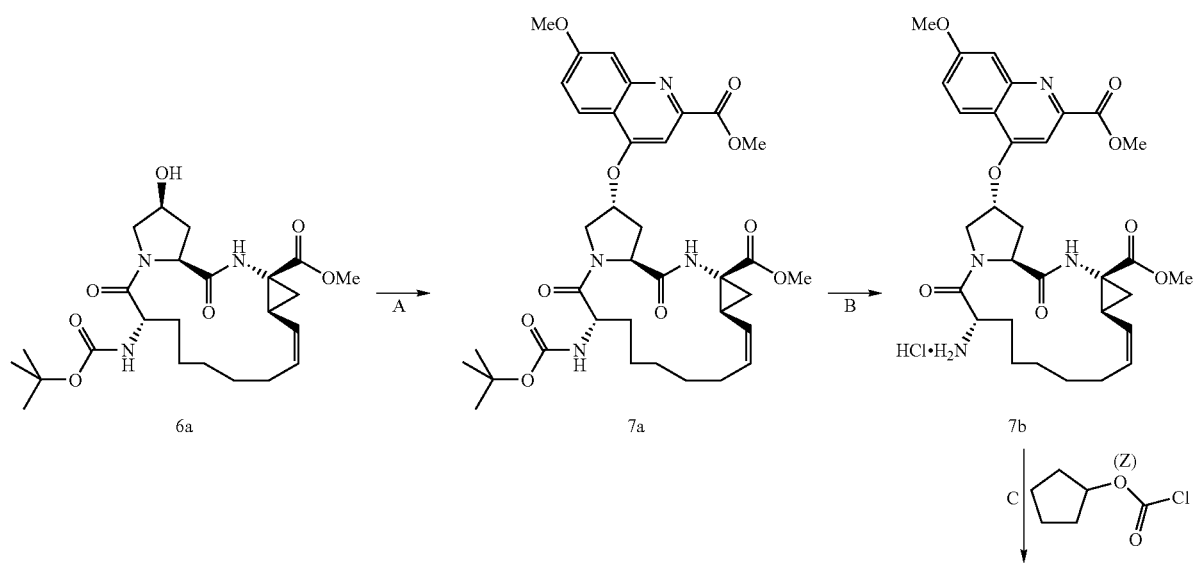

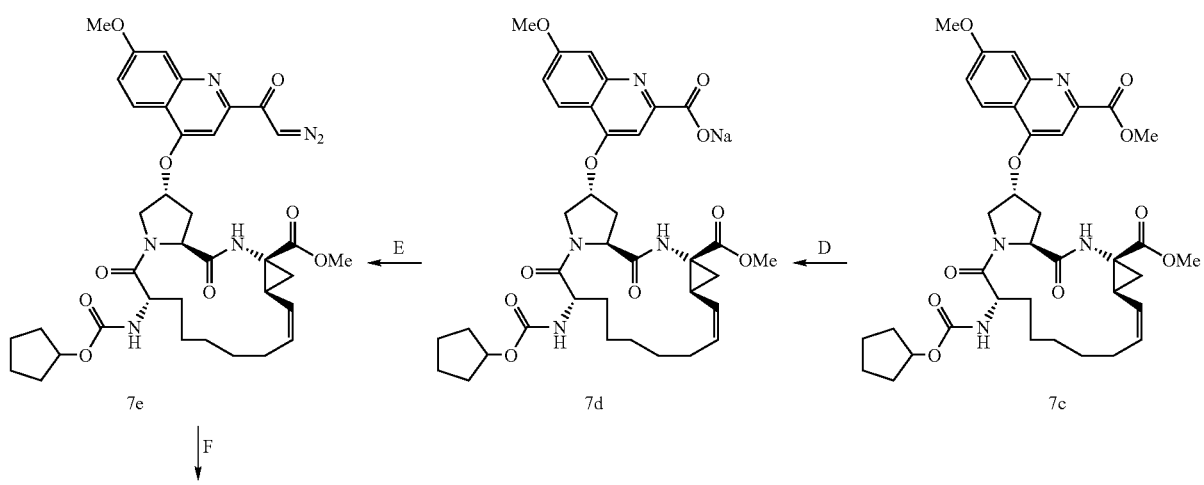

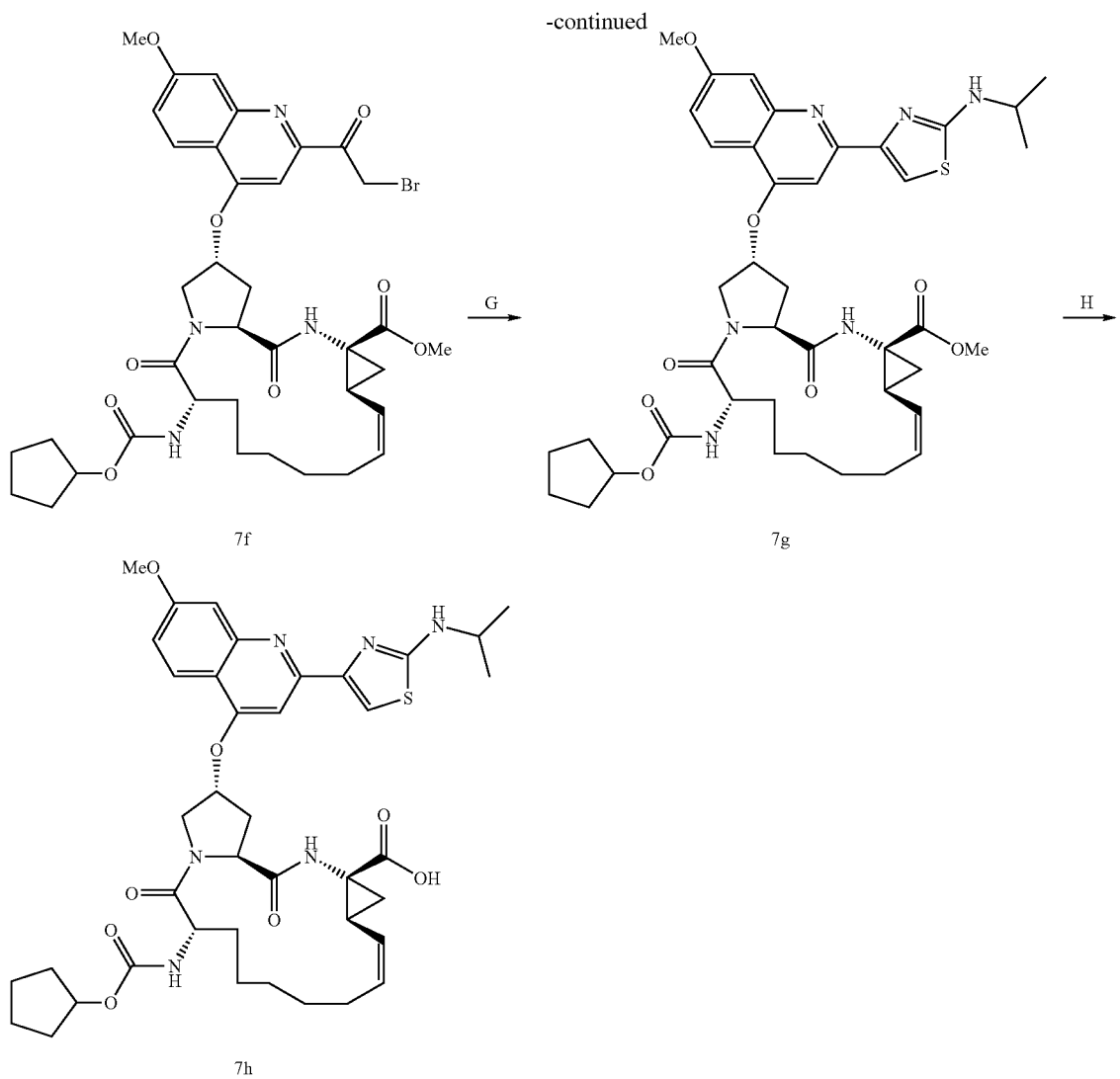

Step A. To a solution of the macrocyclic intermediate 6a (13.05 g, 27.2 mmol, 1.0 eq.), Ph₃P (14.28 g, 54.4 mmol, 2.0 eq) and 2-carboxymethoxy-4-hydroxy-7-methoxyquinoline (WO 00/09543 & WO 00/09558) (6.67 g, 28.6 mmol, 1.05 eq) in THF (450 mL) at 0°, DIAD (10.75 mL, 54.6 mmol, 2.0 eq) was added dropwise over a period of 15 min. The ice bath was then removed and the reaction mixture was stirred at RT for 3 h. After the complete conversion of starting material to products, the solvent was evaporated under vacuum, the remaining mixture diluted with EtOAc, washed with saturated NaHCO₃ (2×) and brine (1×), the organic layer was dried over anhydrous MgSO₄, filtered and evaporated to dryness. Pure compound 7a was obtained after flash column chromatography; the column was eluted first with hexane/EtOAc (50:50), followed by CHCl₃/EtOAc (95:5) to remove Ph₃PO and DIAD byproducts and elution of the impurities was monitored by TLC. Finally, the desired product 7a was eluted from the column with CHCl₃/EtOAc (70:30). Usually, the chromatography step had to be repeated 2-3 times before compound 7a could be isolated in high purity as a white solid with an overall yield of 68% (12.8 g, 99.5% pure by HPLC).

Step B. To a solution of the Boc-protected intermediate 7a (1.567 g) in CH₂Cl₂ (15 mL), 4N HCl in dioxane (12 mL) was added and the reaction mixture was stirred at RT for 1 h. [In the event that a thick gel would form half way through the reaction period, an additional 10 mL CH₂Cl₂ was added.] Upon completion of the deprotection the solvents were evaporated to dryness to obtain a yellow solid and a paste like material. The mixture was redissolved in approximately 5% MeOH in CH₂Cl₂ and re-evaporated to dryness under vacuum to obtain compound 7b as a yellow solid, which was used in the next step without any purification.

Step C. To a solution of cyclopentanol (614 µL, 6.76 mmoL) in THF (15 mL), a solution of phosgene in toluene (1.93M, 5.96 mL, 11.502 mmol) was added dropwise and the mixture was stirred at RT for 2 h to form the cyclopentyl chloroformate reagent (z). After that period, approximately half of the solvent was removed by evaporation under vacuum, the remaining light yellow solution was diluted by the addition of CH₂Cl₂ (5 mL) and concentrated to half of its original volume, in order to assure the removal of all excess phosgene. The above solution of the cyclopentyl chloroformate reagent was further diluted with THF (15 mL) and added to the amine-2 HCl salt 7b. The mixture was cooled to 0° in an ice bath, the pH was adjusted to ~8.5-9 with the addition of Et₃N (added dropwise) and the reaction mixture was stirred at 0° for 1 h. After that period, the mixture was diluted with EtOAc, washed with water (1×), saturated NaHCO₃ (2×), H₂O (2×) and brine (1×). The organic layer was dried over anhydrous MgSO₄, filtered and evaporated under vacuum to obtain a yellow-amber foam. Dimethyl ester 7c was obtained as a white foam after purification by flash column chromatography (using a solvent gradient from 30% hexane to 20% hexane in EtOAc as the eluent) in 80% yield (1.27 g) and >93% purity.

Step D. The dimethyl ester 7c (1.17 g) was dissolved in a mixture of THF/MeOH/H₂O (20 mL, 2:1:1 ratio), and an aqueous solution of NaOH (1.8 mL, 1N, 1 eq.) was added. The reaction mixture was stirred at RT for 1 h before it was evaporated to dryness to obtain the sodium salt 7d as a white solid (~1.66 mmol). Compound 7d was used in the next step without purification.

Step E. The crude sodium salt 7d (1.66 mmoL) was dissolved in THF (17 mL), Et₃N was added and the mixture was cooled to 0° in an ice bath. Isobutylchloroformate (322 µL, 2.5 mmol) was added dropwise and the mixture was stirred at 0° for 75 min. After that period, diazomethane (15 mL) was added and stirring was continued at 0° for 30 min and then at RT for an additional 1 h. Most of the solvent was evaporated to dryness under vacuum, the remaining mixture was diluted with EtOAc, washed with saturated NaHCO₃ (2×), H₂O (2×) and brine (1×), dried over anhydrous MgSO₄, filtered and evaporated to dryness to obtain compound 7e as a light yellow foam (1.2 g, ~1.66 mmol). The diazoketone intermediate 7e was used in the next step without purification.

Step F. The diazoketone 7e (1.2 g, 1.66 mmoL) dissolved in THF (17 mL) was cooled to 0° in an ice bath. A solution of aqueous HBr (48%, 1.24 mL) was added dropwise and the reaction mixture was stirred at 0° for 1 h. The mixture was then diluted with EtOAc, wash with saturated NaHCO₃ (2×), H₂O (2×) and brine (1×), the organic layer was dried over anhydrous MgSO₄, filtered and evaporated to dryness to obtain the α-bromoketone intermediate 7f as a light yellow foam (~1.657 mmol).

Step G. To a solution of the bromoketone 7f (1.66 mmol) in isopropanol (50 mL), isopropylthiourea (392 mg, 3.32 mmol) was added and the reaction mixture was placed in a preheated oil bath at 75° where it was allowed to stir for 1 h. The isopropanol was then removed under vacuum and the product dissolved in EtOAc (250 mL). The solution was washed with saturated NaHCO₃ and brine, the organic layer was dried over anhydrous Na₂SO₄, filtered and evaporated to afford the crude product 7 g (1.35 g) as a cream colored solid. The crude product was purified by flash chromatography in silica gel (1:1 hexane/EtOAc) to afford 860 mg of an off-white solid (66% yield over 4 steps).

Step H. The methyl ester 7g (860 mg, 1.1 mmol) was dissolved in a solution of THF/MeOH/H₂O(2:11, 24 mL) and saponified with LIOH. H₂O(369 mg, 8.8 mmol). The hydrolysis reaction was carried out over 12 h at RT. Thereafter, the solution was evaporated to dryness to give an off-white paste. The paste was diluted with EtOAc and brine. The mixture was adjusted to pH 6 with 1N HCl. The EtOAc layer was separated and the aqueous layer was extracted twice with EtOAc. The combined EtOAc extracts were washed with deionized water (2×) and brine (1×), dried (MgSO₄), and evaporated to afford the cyclic tripeptide intermediate 7 h as a yellow solid (818 mg; 97% yield).

¹H NMR (400 MHz, DMSO-d₆): δ 8.59(s,1H), 8.03(d, J=9 Hz, 1H), 7.43(s,2H), 7.28(d, J=2 Hz, 1H), 7.23 (d, J=6.7 Hz, 1H), 7.02 (dd, J=1.9, 8.9 Hz, 1H), 5.54-5.41 (m, 2H), 5.28 (bdd, J=9.2, 9.2 Hz,1H), 4.73-4.64 (m, 1H), 4.54-4.42 (m, 2H), 4.17-4.08 (m,1H), 3.96-3.91 (m,1H), 3.90 (s, 3H), 3.86-3.76 (m, 1H), 2.60-2.44 (m, 1H), 2.43-2.31 (m,1H), 2.23-2.13 (m, 1H), 1.82-1.28 (m, 20H), 1.26 (d, J=1.3 Hz, 3M), 1.24 (d, J=1.3 Hz, 3H).

Example 8

Preparation of Compound 100 (Compound of Formula I wherein R¹ is Methyl)

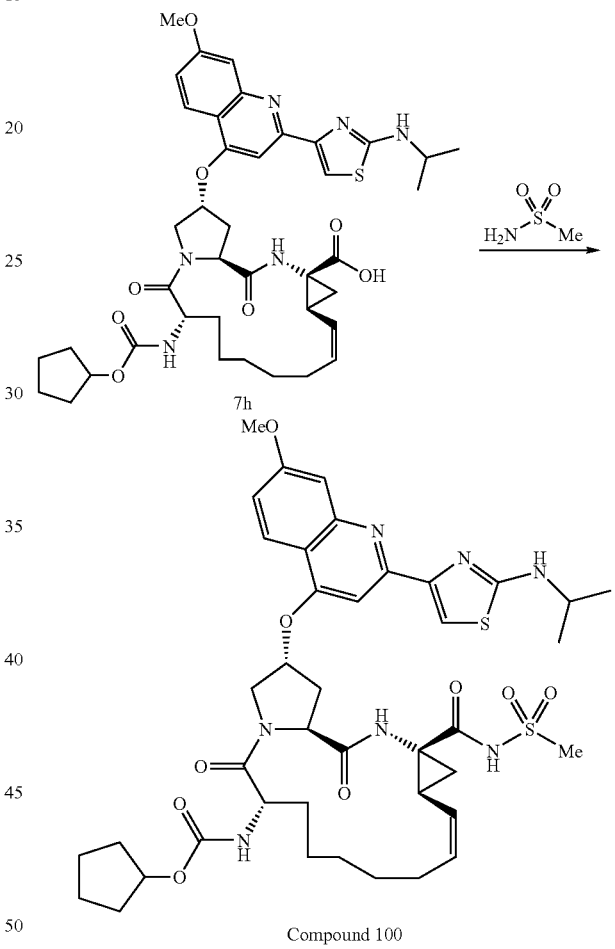

The cyclic tripeptide intermediate 7h (20 mg, 0.026 mmol) was combined with HATU (12 mg, 0.031 mmol) in anhydrous DMF (4 mL). The solution was stirred at R.T. before DIPEA (23 µL, 0.13 mmol) was added dropwise over ca. 1 min. The mixture was stirred for 40 min. at R.T. and analyzed by analytical HPLC for the formation of the activated ester. A solution of methanesulfonamide (12.4 mg, 0.13 mmol), DMAP (14.3 mg, 0.12 mmol) and DBU (15.5 µL, 0.10 mmol) were added in DMF (1 mL). The reaction mixture was stirred 36 hr at R.T. before being concentrated. The residue was reconstituted in DMSO and purified by preparative HPLC. Lyophilization of pure fractions gave the sulfonamide derivative 100 (7.95 mg, 36%) as a bright yellow amorphous solid.

MS (electrospray): 852.5 (M+H)+, and 850.5 (M−H)−.

RP-HPLC: Rt=6.6 minutes (homogeneity=100%).

Example 9

Preparation of Compound 101 (Compound of Formula I wherein $R^1$ is phenyl)

Compound 101

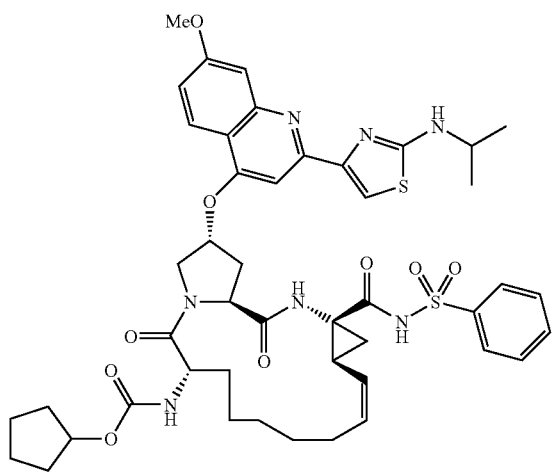

Using the same protocol as described in example 8 except using benzenesulfonamide instead of methanesulfonamide, the phenyl analog 101 was prepared as a bright yellow amorphous solid in 27% yield.

MS (electrospray); 914.5 (M+H)+, and 912.5 (M−H)−.
RP-HPLC: Rt=7.2 minutes (homogeneity=100 %).

Example 10

Preparation of Compound 102 (Compound of Formula I wherein $R^1$ is Cyclopropyl)

Compound 102

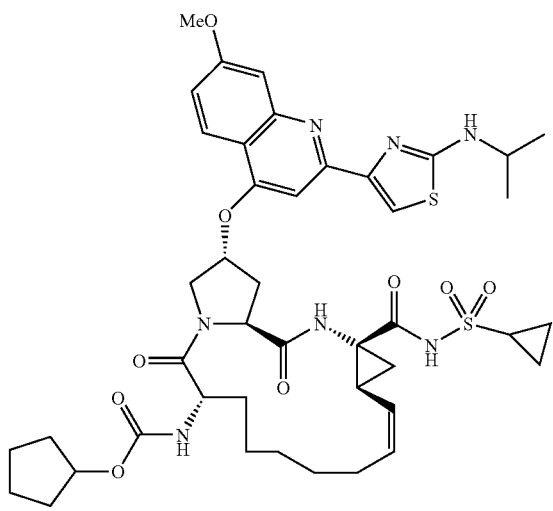

The cyclic tripeptide intermediate 7h (20 mg, 0.026 mmol) was combined with HATU (29.5 mg, 0.077 mmol) in anhydrous DMF (4 mL). The solution was stirred at R.T. before DIPEA (23 µL, 0.13 mmol) was added dropwise over ca. 1 min. The mixture was stirred for 45 minutes at R.T. and analyzed by analytical HPLC for the formation of the activated ester at 6.6 minutes.

Next, a solution of the cyclopropanesulfonamide (12.6 mg, 0.104 mmol), DMAP (14.3 mg, 0.117 mmol) was added all at once in DMF (1 mL). After 2 hr, DBU (15.5 mL, 0.104 mmol) was added and the reaction mixture stirred 20 h at R.T. before being concentrated. The reaction was reconstituted in DMSO and purified by preparative HPLC. Lyophilization of pure fractions gave the sulfonamide derivative 102 as a yellow solid (6.5 mg, 28.5%).

MS (electrospray); 878.4 (M+H)+, and 876.4 (M−H)−.
RP-HPLC: Rt=6.9 minutes (homogeneity=100%).

Biological Assays

NS3-NS4A Protease Assay

The enzymatic assay used to evaluate the present compounds is described in WO 00/09543 and WO 00/59929.

Cell Based HCV RNA Replication Assay

The cell-based HCV RNA replication assay used to evaluate the present compounds is described in detail in WO03/010141.

Some of the compounds of this invention were evaluated the preceding enzymatic and cell based assays and were found to be highly active. More specifically, the compounds had $IC_{50}$'s below 0.1 µM in the NS3-NS4A protease assay, and $EC_{50}$'s below 0.5 µM in the cell based HCV RNA replication assay.

Specific Assays

The specificity assays used to evaluate the selectivity of this compound are described in WO 00/09543.

When the compounds were evaluated in the specificity assays, the compounds of formula I were found to be selective in that they do not show significant inhibition in the Human Leukocyte Elastase and Cathepsin B assays.

Table of compounds

| Compound # | $R^1$ |
|---|---|
| 100 | methyl |
| 101 | phenyl |
| 102 | cyclopropyl |
| 103 | ethyl |
| 104 | i-propyl |
| 105 | n-propyl |
| 106 | n-butyl |
| 107 | sec-butyl |

-continued

Table of compounds

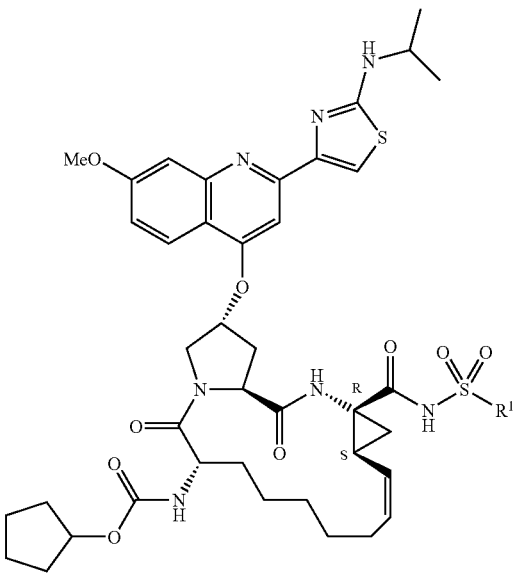

| Compound # | R¹ |
|---|---|
| 108 | n-pentyl |
| 109 | 2-Me-butyl |
| 110 | 3-Me-butyl |
| 111 | cyclobutyl |
| 112 | cyclopentyl |
| 113 | —CH₂-cyclopropyl |
| 114 | —CH₂—CH₂-cyclohexyl |
| 115 | CCl₃ |
| 116 | CF₃ |
| 117 | 2-fluorophenyl |
| 118 | 4-methylphenyl |
| 119 | 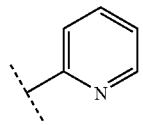 |
| 120 | 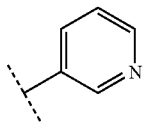 |
| 121 | 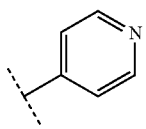 |
| 122 | 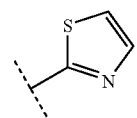 |
| 123 | 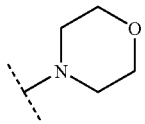 |

-continued

Table of compounds

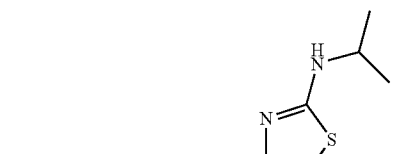

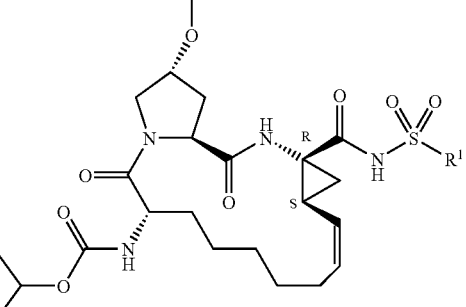

| Compound # | R¹ |
|---|---|
| 124 | 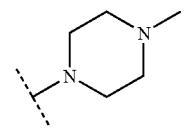 |

What is claimed is:

1. A compound of formula (I)

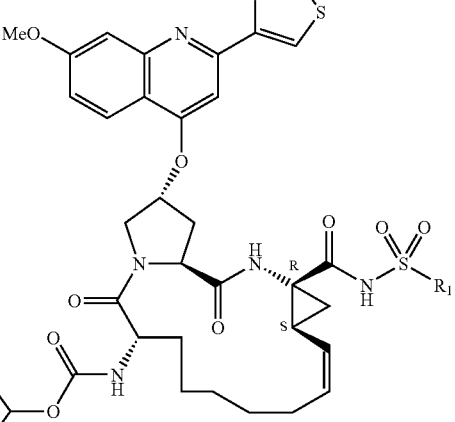

wherein R¹ is $(C_{3-7})$cycloalkyl-$(C_{1-6})$alkylene or Het, which are all optionally substituted from 1 to 3 times with halo, cyano, nitro, O—$(C_{1-6})$alkyl, amido, amino or phenyl; or R¹ is $C_6$ or $C_{10}$ aryl which is optionally substituted from 1 to 3 times with halo, cyano, nitro, $(C_{1-6})$ alkyl, O—(C$_{1-6}$)alkyl, amido, amino or phenyl; or a pharmaceutically acceptable salt thereof.

2. A compound according to claim 1, wherein said Het is:

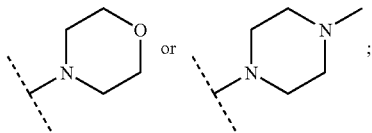

or a heteroaryl selected from:

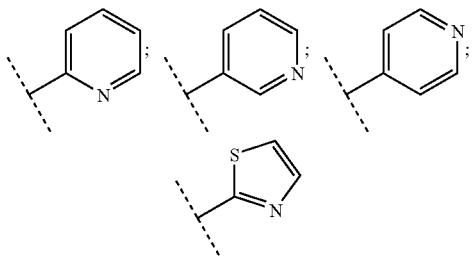

said heteroaryl being optionally substituted with C$_{1-6}$ alkyl.

3. A compound according to claim 1, wherein R$^1$ is (C$_{3-7}$) cycloalkyl-(C$_{1-6}$)alkylene, optionally substituted from 1 to 3 times with halo, cyano, nitro, O—(C$_{1-6}$)alkyl, amido, amino or phenyl; or R$^1$ is C$_6$ or C$_{10}$ aryl which is optionally substituted from 1 to 3 times with halo, cyano, nitro, (C$_{1-6}$)alkyl, O—(C$_{1-6}$)alkyl, amido, amino or phenyl; or a pharmaceutically acceptable salt thereof.

4. A compound according to claim 3, wherein R$^1$ is (C$_{3-7}$) cycloalkyl-(C$_{1-6}$)alkylene, optionally substituted from 1 to 3 times with halo, nitro or O—(C$_{1-6}$)alkyl, or R$^1$ is phenyl which is optionally substituted from 1 to 3 times with halo, nitro, (C$_{1-6}$)alkyl or O—(C$_{1-6}$)alkyl.

5. A compound according to claim 4, wherein R$^1$ is cyclopropylmethyl, cyclohexylethyl, phenyl, 2-fluorophenyl, or 4-methylphenyl.

6. A compound according to claim 5 wherein R$^1$ is phenyl.

7. A pharmaceutical composition comprising an anti-hepatitis C virally effective amount of a compound of formula I according to claim 1, or a pharmaceutically acceptable salt thereof, in admixture with a pharmaceutically acceptable carrier medium or auxiliary agent.

8. A pharmaceutical composition according to claim 7, further comprising a therapeutically effective amount α-interferon.

9. A pharmaceutical composition according to claim 7, further comprising a therapeutically effective amount of pegylated α-interferon.

10. A pharmaceutical composition according to claim 7, further comprising a therapeutically effective amount of ribavirin.

11. A pharmaceutical composition according to claim 8, further comprising a therapeutically effective amount of ribavirin.

12. A pharmaceutical composition according to claim 9, further comprising a therapeutically effective amount of ribavirin.

13. A method of treating a hepatitis C viral infection in a mammal comprising administering to the mammal an anti-hepatitis C virally effective amount of a compound of formula I according to claim 1, or a pharmaceutically acceptable salt thereof.

14. A method of treating a hepatitis C viral infection in a mammal comprising administering to the mammal an anti-hepatitis C virally effective amount of the composition according to claim 7.

15. A method of treating a hepatitis C viral infection in a mammal comprising administering to the mammal an anti-hepatitis C virally effective amount of the composition according to claim 8.

16. A method of treating a hepatitis C viral infection in a mammal comprising administering to the mammal an anti-hepatitis C virally effective amount of the composition according to claim 9.

17. A method of treating a hepatitis C viral infection in a mammal comprising administering to the mammal an anti-hepatitis C virally effective amount of the composition according to claim 10.

18. A method of inhibiting the replication of hepatitis C virus comprising exposing the virus to a hepatitis C viral NS3 protease inhibiting amount of a compound of formula I according to claim 1, or a pharmaceutically acceptable salt thereof.

19. A method of treating a hepatitis C viral infection in a mammal comprising administering to the mammal an anti-hepatitis C virally effective amount of a pharmaceutical composition comprising a compound of formula I according to claim 1, or a pharmaceutically acceptable salt thereof, and one or more other anti-HCV agents.

20. A method according to claim 19, wherein said other anti-HCV agent is selected from the group consisting of: α-, β-δ-, γ-, ω-interferon, pegylated α-, β, δ, γ-, ω-interferon, ribavirin and amantadine.

21. A method according to claim 20, wherein said other anti-HCV agent is α-interferon.

22. A method according to claim 20, wherein said other anti-HCV agent is pegylated α-interferon.

23. A method according to claim 21, wherein the composition further comprises ribavirin.

24. A method according to claim 22, wherein the composition further comprises ribavirin.

25. A method of treating a hepatitis C viral infection in a mammal comprising administering to the mammal an anti-hepatitis C virally effective amount of a combination of a compound of formula I according to claim 1, or a pharmaceutically acceptable salt thereof, and one or more other anti-HCV agents, wherein said one or more other anti-HCV agents are administered to the mammal prior to, concurrently with, or following the administration of the compound of formula I.

* * * * *

UNITED STATES PATENT AND TRADEMARK OFFICE
CERTIFICATE OF CORRECTION

| | | |
|---|---|---|
| PATENT NO. | : 7,504,378 B2 | Page 1 of 1 |
| APPLICATION NO. | : 11/298443 | |
| DATED | : March 17, 2009 | |
| INVENTOR(S) | : Llinas-Brunet et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 429 days.

Signed and Sealed this

Sixteenth Day of November, 2010

David J. Kappos
*Director of the United States Patent and Trademark Office*